(12) United States Patent
Lubs et al.

(10) Patent No.: US 7,328,794 B2
(45) Date of Patent: Feb. 12, 2008

(54) PACKAGING FOR ELONGATE MEDICAL DEVICES AND METHODS OF MANUFACTURE AND USE THEREOF

(75) Inventors: Jason M. Lubs, Maple Grove, MN (US); Benjamin Prusi, Blaine, MN (US); Jeff Velander, Mound, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 597 days.

(21) Appl. No.: 10/794,152

(22) Filed: Mar. 5, 2004

(65) Prior Publication Data

US 2005/0194276 A1    Sep. 8, 2005

(51) Int. Cl.
*B65D 85/20* (2006.01)
(52) U.S. Cl. .................................... 206/364
(58) Field of Classification Search ............. 206/364, 206/363, 365, 476, 477, 478, 482, 483, 486, 206/487, 488, 489
See application file for complete search history.

(56) References Cited

U.S. PATENT DOCUMENTS

| | | | |
|---|---|---|---|
| 1,304,231 A | | 5/1919 | Wilson |
| 2,135,134 A | * | 11/1938 | Ehlers ..................... 206/728 |
| 3,411,620 A | | 11/1968 | Steinbock |
| 3,460,742 A | | 8/1969 | Langdon |
| 3,556,294 A | | 1/1971 | Walck, III et al. |
| 3,612,038 A | | 10/1971 | Halligan |
| 3,633,758 A | | 1/1972 | Morse et al. |
| 3,677,250 A | | 7/1972 | Thomas |
| 3,750,875 A | | 8/1973 | Juster |

(Continued)

FOREIGN PATENT DOCUMENTS

EP       0 423 855 B1    4/1991

(Continued)

OTHER PUBLICATIONS

Illustrations for Packaging Card design sent by applicant Feb. 26, 2004.

*Primary Examiner*—Mickey Yu
*Assistant Examiner*—Jerrold Johnson
(74) *Attorney, Agent, or Firm*—Crompton, Seager & Tufte, LLC (57) ABSTRACT

Packaging units for use with elongate medical devices such as catheters. An example packaging unit includes a mounting card into which a number of tabs are cut at predetermined angles and shapes. At least some of the tabs are provided in large tab/small tab pairs. The angle and size combination provides for securing the elongate medical device to the card, while reducing trauma experienced by the device during removal from the card. Also, a double tab system is provided in the packaging unit for receiving a hub and strain relief to hold those parts securely. The card may be scored along at least a first side such that, prior to placing a sterile barrier, such as a plastic wrapping or envelope, around the mounting card to sterilely seal a device therein, the card may be bent along the scoring line to lift the sterile barrier off of a surface of the mounting card. The step of bending a portion of the card along the storing line make removal of a device from the mounting card easier and renders the mounting card more rigid and less likely to bend and cause damage to an elongate medical device stored thereon.

27 Claims, 4 Drawing Sheets

U.S. PATENT DOCUMENTS

| | | | |
|---|---|---|---|
| 3,927,762 A | | 12/1975 | Zdarsky et al. |
| 3,930,580 A | | 1/1976 | Bazell et al. |
| 3,967,728 A | | 7/1976 | Gordon et al. |
| 4,019,633 A | | 4/1977 | Roth |
| 4,023,678 A | * | 5/1977 | Fiedler ................. 206/363 |
| 4,121,711 A | * | 10/1978 | Bolanowski ............ 206/63.3 |
| 4,134,493 A | * | 1/1979 | Cech ..................... 206/756 |
| 4,306,656 A | | 12/1981 | Dahlem |
| 4,332,322 A | * | 6/1982 | Jaeschke et al. ........ 206/364 |
| 4,367,816 A | | 1/1983 | Wilkes |
| 4,563,177 A | | 1/1986 | Kamen |
| 4,779,727 A | | 10/1988 | Taterka et al. |
| 4,923,061 A | | 5/1990 | Trombley, III |
| 4,925,448 A | | 5/1990 | Bazaral |
| 4,936,464 A | | 6/1990 | Kim |
| 5,105,942 A | | 4/1992 | van Veen et al. |
| 5,131,537 A | | 7/1992 | Gonzalez |
| 5,165,540 A | | 11/1992 | Forney |
| 5,341,823 A | * | 8/1994 | Manosalva et al. ...... 128/898 |
| 5,351,822 A | | 10/1994 | Sinn |
| 5,375,717 A | | 12/1994 | Roshdy |
| 5,392,918 A | | 2/1995 | Harrison |
| 5,402,886 A | | 4/1995 | McGlinch |
| 5,447,231 A | | 9/1995 | Kastenhofer |
| 5,467,873 A | * | 11/1995 | Kastenhofer ............ 206/363 |
| 5,497,601 A | | 3/1996 | Gonzalez |
| 5,501,341 A | | 3/1996 | Van Es |
| 5,699,909 A | | 12/1997 | Foster |
| 5,772,031 A | | 6/1998 | Landis |
| 5,848,691 A | | 12/1998 | Morris et al. |
| 5,947,296 A | | 9/1999 | Castora |
| 6,009,998 A | | 1/2000 | Webinger |
| 6,053,313 A | | 4/2000 | Farrell et al. |
| 6,053,905 A | | 4/2000 | Daignault, Jr. et al. |
| 6,068,121 A | | 5/2000 | McGlinch |
| 6,074,368 A | | 6/2000 | Wright |
| 6,090,076 A | | 7/2000 | Lane, Jr. |
| 6,543,615 B2 | | 4/2003 | Lake |
| 2002/0066685 A1 | | 6/2002 | Leitch |
| 2004/0004014 A1 | | 1/2004 | Grossman |
| 2004/0055919 A1 | * | 3/2004 | Rowe et al. ............. 206/438 |

FOREIGN PATENT DOCUMENTS

| | | |
|---|---|---|
| EP | 0 440 427 B1 | 8/1991 |
| EP | 0 602 965 A2 | 6/1994 |
| EP | 0 667 170 A1 | 8/1995 |
| EP | 0 739 641 A1 | 10/1996 |
| JP | 2000255627 | 9/2000 |
| WO | WO 98/58697 | 12/1998 |

* cited by examiner

PACKAGING FOR ELONGATE MEDICAL DEVICES AND METHODS OF MANUFACTURE AND USE THEREOF

TECHNICAL FIELD

The present invention generally relates to the field of medical device packaging, and more specifically to the field of packaging catheters and other similar medical devices.

BACKGROUND

Numerous medical procedures require the advancement and positioning of elongate medical devices within body lumens. Intravascular catheters, in particular, are currently utilized in a wide variety of minimally invasive medical procedures. Such catheters often have an outer diameter in the range of two or less millimeters near their distal ends. The distal ends are often also highly flexible and may include softened distal tips. Further, some devices (coronary guide catheters, for example) include a formed distal end having a predefined curve adapted to interact in a desired manner with patient anatomy. Packaging these catheters for delivery and/or storage entails a number of concerns.

One packaging technique for catheters includes the use of a mounting card. Mounting cards are generally long, somewhat narrow (100+cm by 10-20 cm) cards having a plurality of die-cut tabs that hold the catheter in place. These die-cut tabs are usually created using a manual press that cuts the specific shape of the tab into the mounting card. Once the tabs are cut, the tabs are then raised, allowing the catheter to be woven under the tabs. The tabs are then released and deflect back toward the mounting card, such that the catheter to be held in place by the tabs' downward pressure. One in the art generally knows this weaving procedure as "webbing."

Once mounted on the card, the catheter and mounting card are then wrapped in a sterile barrier, sometimes known as an envelope, and then sealed. The sterile barrier may also be secured down to the card at chosen locations.

Physicians have found that catheters fastened by tabs sometimes succumb to physical deformation during the catheter's removal. With the sterile barrier placed over and around the catheter and mounting card, the catheter is typically removed by simple pulling the catheter through the tabs. Because the distal end is generally the most flexible region of the catheter, the distal end may be deformed and/or kinked quite readily. Pulling the device through a tab may easily impart a new structural formation to the catheter that was not desired by the manufacturer. A further difficulty can arise because the sterile barrier touches the catheter itself, creating additional friction during catheter removal. Extra force is then required to remove the catheter, again subjecting portions of the catheter shaft to stresses that may lead to deformation and/or kinking.

Also, because the sterile barrier is often provided such that it holds the catheter against the catheter holding card, the canting (out of plane curvature) provided in certain catheter types can become distorted or damaged either during removal, or during storage and shipping. For example, certain guiding catheters for accessing the aortic arch include curvatures at their distal ends which do not lie in a single plane. Thus, when placed on a generally flat catheter holding card and pressed down on the card, these catheters may lose their desired shape and become less suitable for their intended purpose. Each of these are examples of damage that can result with known catheter packaging systems. There is an ongoing need to provide alternative designs and methods of making and using packaging for medical devices.

SUMMARY

The invention relates to alternative designs and methods of making and using packaging for medical devices. One example embodiment relates to a catheter packaging unit which includes a mounting card into which a number of tabs are cut at predetermined angles and shapes. At least some of the tabs are provided in large tab/small tab pairs. The angle and size combination provides for securing the catheter to the mounting card, while reducing the trauma experienced by the catheter during removal from the mounting card. Some example embodiments relate to a mounting card that may be scored along at least a first side such that, prior to placing a sterile barrier (for example, a plastic wrapping) around the package to seal a catheter therein, the mounting card may be bent along the scoring line to lift the sterile barrier off of a surface of the card, preventing damage to a catheter stored therein. In yet a further embodiment, a double tab system is provided in the catheter packaging unit for receiving a catheter manifold and hold that portion of a catheter securely.

The above summary of some embodiments is not intended to describe each disclosed embodiment or every implementation of the present invention. The Figures, and Detailed Description which follow more particularly exemplify these embodiments.

BRIEF DESCRIPTION OF THE FIGURES

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following detailed description should be read with reference to the drawings. The drawings, which are not necessarily to scale, depict illustrative embodiments and are not intended to limit the scope of the invention.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Several of the embodiments illustrated herein are the result of an arduous testing process. It was noted that with some existing catheter packaging units, a variety of deformations and even kinking of catheter shafts were occurring during shipping of packaged units and removal of catheters from such units. In order to identify structures that were better and/or worse with respect to these problems, a number of tests were performed.

One such test made use of a high speed camera to observe the "whipping" of the distal end of a catheter as it was removed from packaging. In some systems using tabs or other structures to hold a catheter to a mounting card, as the catheter is removed the highly flexible distal end of the catheter will be bent and/or stressed during such removal. Several catheters, for example guide catheters, have specially curved distal ends. As the catheter distal end moves past a tab or other structure, its predefined curve may be straightened or otherwise stressed out of shape. When the distal end clears the tab, it will flex back towards its original shape. This movement can be referred to as "whipping". If there is a large amount of whip, it indicates a greater stress on the catheter shaft. One goal in the design of the following illustrative embodiments was to reduce such whipping.

By observing catheter removals with the high speed camera, comparisons were made among several selected designs. It was found that certain tab combinations performed quite well. A particularly successful configuration was that of a combination of large and small tabs.

Figure 1:
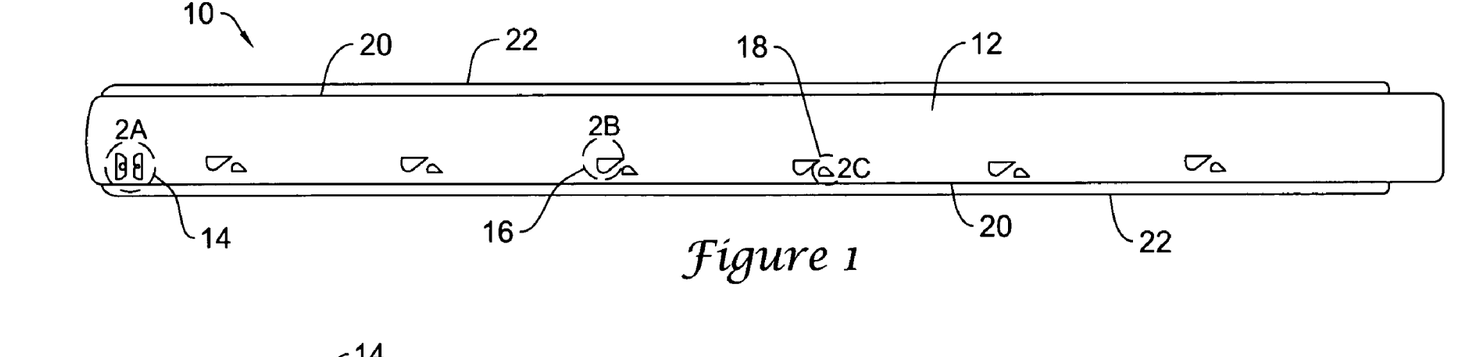
FIG. 1 shows an elevation view of an illustrative example catheter mounting card.

FIG. 1 shows an elevation view of an illustrative catheter mounting card. The catheter mounting card 10 may be formed primarily with a generally planar piece of relatively stiff material shown as a planar piece 12. The planar piece 12 may be formed, for example, of a paperboard product such as a solid unbleached sulfate, a clay coated new back, solid bleached sulfate, solid fiber, or any other suitable material.

The planar piece 12 may have any desired thickness, for example, in the range of about 8 pt to 30 pt thickness. In some embodiments the planar piece 12 may or may not include at least one glossy side, and may be used with or without the glossy side up. The planar piece 12 may have a length chosen for suitability for use with a catheter of a certain size. For example, with a generally straight catheter having a length of one hundred ten to one hundred twenty five centimeters, the planar piece 12 may have an overall length in the range of about one hundred forty centimeters. Further, the width of the planar piece 12 may have a width chosen for suitability and compactness; for example, the width may be in the range of about five to twenty centimeters. For most cases it is sufficient to have a width of about eleven centimeters. The ranges given above, of course, will be understood by one of skill in the art as merely illustrative, and thickness, length, and width of the planar piece 12 may vary as desired. In particular, for shorter catheters (for example down to fifty cm or less), the planar piece 12 may much shorter.

A number of structures are defined in the planar piece 12 including hub securing tabs 14, a number of large tabs 16 and small tabs 18, and a pair of scored lines 20. The "large" and "small" tabs 16, 18 are described in such terms as being sized relative to one another, and this use of terminology should not be taken as implying a particular range. The large tabs 16 and small tabs 18 are arranged along a line for receiving a catheter on the planar piece 12.

Along the length of the planar piece 12, two scored lines 20 are included, being cut into the surface of the planar piece 12 near its long edges 22. The scored lines 20 make it easy to fold up the edges 22 of the planar piece 12. It can be seen that the planar piece 12 may be shaped so that the scored lines 20 do not extend to either extreme end of the catheter mounting card 10. When the edges are folded up, as shown below in FIG. 9, a sterile barrier can be suspended over the planar piece 12 as well as the hub securing tabs 14 and the large/small tabs 16, 18 so that the sterile barrier does not compress a catheter packaged with the catheter mounting card 10. Further, by folding up the edges, the planar piece 12 may be given added rigidity, preventing kinking of the catheter due to bending of the planar piece 12 during handling, shipping, or storage. As an alternative to folding up the edges, one may also place one or more corrugations extending axially on the planar piece away form the edges thereof.

Each of the pieces in FIGS. 1 and 2A-2C may be cut into the planar piece 12 by any suitable method, for example, by die cutting. The individual tabs may be formed by cutting entirely through the planar piece 12 along the lines which fold out and away form the planar piece 12. The folding line allowing the tabs (lines 40 shown in each of FIGS. 2A-2C) to be folded out of the planar piece 12 may be scored on either or both sides of the planar piece 12, as desired.

As explained above, a number of tests were performed using different tab sizes, placements, size combinations, and so forth. During this testing it was found that certain size combinations and angles performed better than others. Details of some of the better combinations, shapes and angles are further explained below with reference to FIGS. 2A-2C.

Figure 2A:
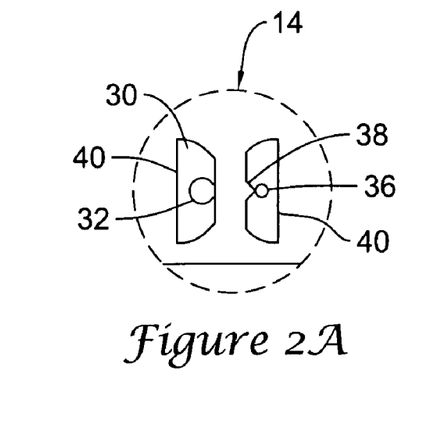
FIG. 2A shows a detail view of an example manifold holding tab configuration.
Figure 8:
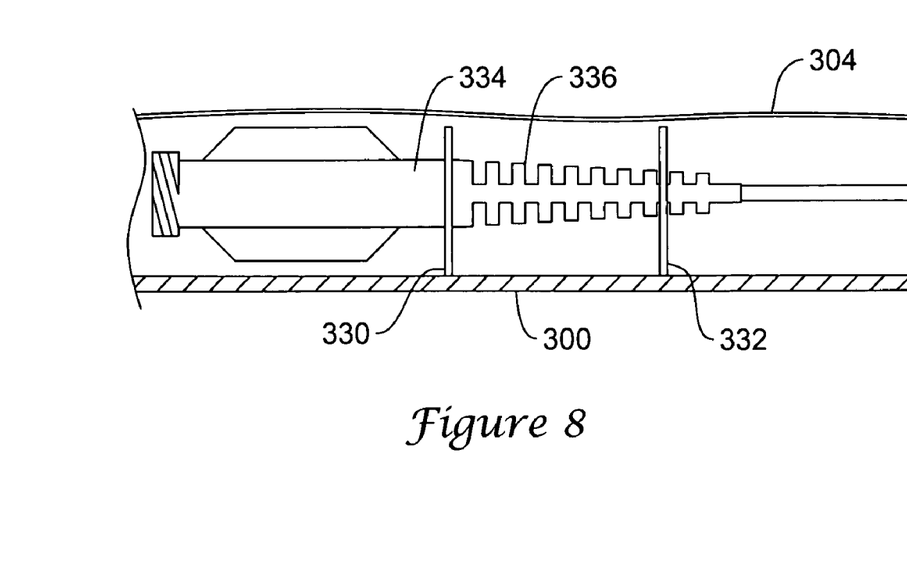
FIG. 8 is a detail view of the example catheter hub holder of FIG. 7.

The design for the hub securing tabs 14 is further explained with reference to FIG. 2A, which shows a detail view of a hub holding tab configuration, as well as FIG. 8, below. As shown in FIG. 2A, the hub securing tabs 14 include a first tab 30 having a semicircular cutout 32 for receiving a cylindrical portion of a catheter hub. An embodiment is further illustrated in FIG. 8, where the sizes and spacing for the first and second hub securing tabs 30, 34 are further explained. It should be noted that for the purposes herein, the word "hub" can be inclusive of a variety of manifolds and hubs including but not limited to a single port hub as shown in FIG. 8, but also Y-shaped manifolds and hubs, multiport hubs, and the like. The hub securing tabs 14 also include a second tab 34 having a circular cut-out 36 and a notch 38. The notch 38 and circular cut-out 36 are adapted for receiving a more distal portion of the hub. For example, the hub may include a ribbed, spiral, or finned strain relief for an attached catheter shaft. The first tab 30 and second tab 34 are spaced from one another sufficiently to allow easy placement of a portion of catheter hub/manifold therebetween. For example, an illustrative embodiment has the first tab 30 about two and a half centimeters from the second tab 34, as further explained below with reference to FIG. 5. This distance may vary, of course, depending on the particular catheter hub and strain relief to be held.

While the securing tabs 14 shown in FIG. 2A are adapted for use with a generally cylindrical catheter hub/manifold, this is not necessary, as the tabs may include openings or spaces for receiving polygonal, semicircular, oval, or other shapes as well. Further, while the example embodiment of FIG. 2A illustrates a notch 38 adapted for receiving a portion of a strain relief, in other embodiments the notch 38 may be adapted to receive other portions of a hub/manifold/strain relief.

Figure 2B:
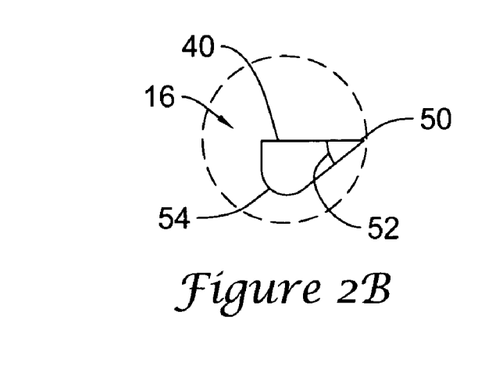
FIG. 2B shows a detail view of an example relatively large tab from FIG. 1.

FIG. 2B shows a detail view of a relatively large tab from FIG. 1. The large tab 16 includes a leading corner 50 and has a generally triangular form such that an angle 52 is formed at the leading corner 50. The corner 54 can form a vertex of the large tab 16 and may be radiused to remove any sharp edges that can damage a catheter or breach a sterile barrier disposed over the large tab 16. The testing performed showed that very good results could be had with an angle 52 of about thirty-eight degrees, or in a range of about thirty to forty five degrees, or in a range of about thirty-six to forty degrees. Overall, the tab length along the bending line 40 may vary as desired, particularly depending upon the size of the catheter to be held in place.

Figure 2C:
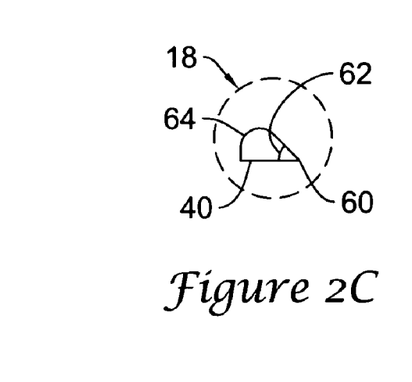
FIG. 2C shows a detail view of an example relatively small tab from FIG. 1.

FIG. 2C shows a detail view of a relatively small tab 18 from FIG. 1. The small tab 18 includes a leading corner 60 and also has a generally triangular shape forming an angle 62 at the leading corner 60. A corner can form a vertex of the small tab 18 and may be radiused as shown at 64 to eliminate any sharp edges that could damage a catheter or breach a sterile barrier used in packaging a catheter. The testing noted above found that improved results could be had with an angle 62 of about forty-five degrees, as well as in ranges of about forty to fifty degrees or forty-three to forty-seven degrees. Again, the tab length along the bending line 40 may vary as desired, to some extent depending upon the size (French) of the catheter to be held in place. The example ranges that are referred to herein are examples of those wherein "whipping" of a catheter being removed past the large tabs 16 and small tabs 18 was reduced in comparison with other tab sizes and combinations.

In an illustrative working embodiment, the large tab 16 has a length along the fold line 40 of about 2.6 centimeters, while the small tab 18 has a length along the fold line 40 of about 1.5 centimeters, with a tolerance in manufacturing of about 1.5 millimeters for either. This illustrative embodiment used an angle 52 for the large tab 16 of about thirty-eight degrees, and an angle 62 for the small tab 18 of about forty-five degrees, and illustrated very good performance in the above described "whip" testing.

The relative sizes for the large tabs 16 and small tabs 18 may also add to the effectiveness of the overall device; as noted, a ratio of about 1.75 to 1.0 (large tab 16 to small tab 18) is included in the illustrative embodiment. Ratios in the range of about 1.5 to 2.0 to 1.0 are considered advantageous. Furthermore, in some embodiments, the relationship between the angles used may be significant to achieve the results noted above, with a combination small tab/large tab wherein the small tab has a larger angle than the large tab being a positive design feature in at least some embodiments.

Figure 3:
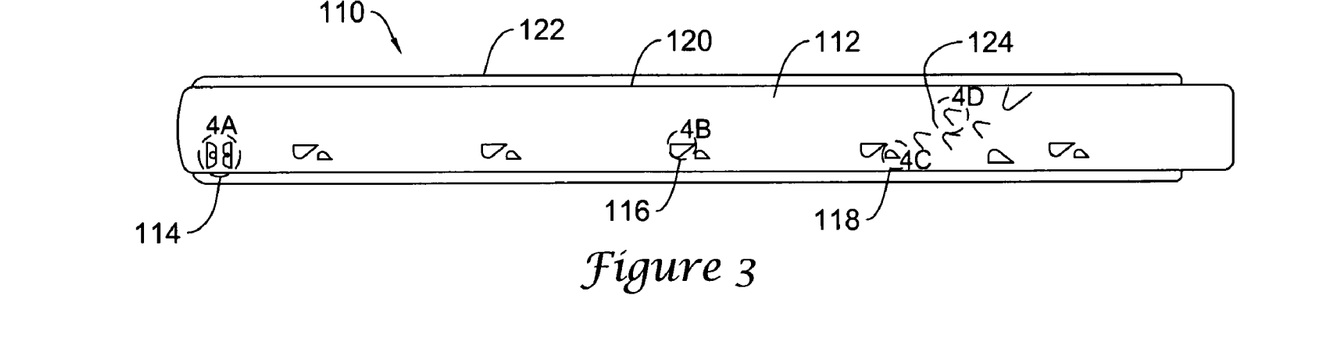
FIG. 3 shows an elevation view of another illustrative example catheter mounting card adapted for receiving and holding catheters of various sizes having curved distal ends.

FIG. 3 shows an elevation view of another illustrative catheter mounting card adapted for receiving and holding catheters of various sizes having curved distal ends. The catheter mounting board 110 includes a generally planar piece 112, on which are formed a hub securing tabs 114, large tabs 116, small tabs 118, scoring lines 120 defining edge portions 122, and a number of curve tabs 124. The overall length of the mounting card 110 may vary widely depending on the size of catheter for which it is designed. One illustrative example has a length of about one-hundred and ten centimeters, with the edge portions 122 ending about 5.5 centimeters from the end opposite the hub securing 114.

Figure 4A:
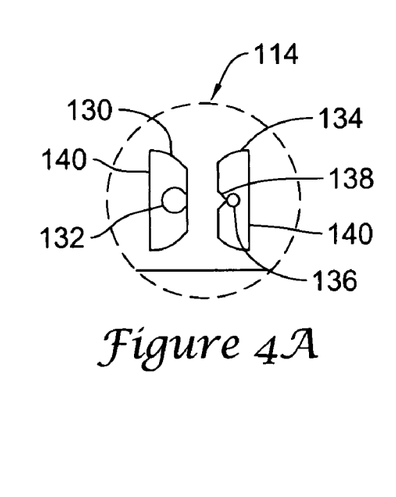
FIG. 4A shows a detail view of an example hub holding tab configuration.

FIG. 4A shows a detail view of a hub holding tab configuration. The hub holding tabs 114 again include a first tab 130 having a circular cut-out 132 and a second tab 134 having a circular cut-out 136 and a notch 138. Each tab 130, 134 maybe folded upward and away form the planar piece along a folding line 140 which may, again, be scored if desired to render the folding easier and more readily defined along a straight line. The configuration is generally similar to that of FIG. 2A. Again, while a circular design is illustrated, it should be apparent to one of skill in the art that non-circular formations may also be used to match the design of a catheter hub, manifold, or strain relief.

It should be noted that scoring the folding lines for the tabs will make the folding line more flexible, reducing the force on the catheter. While this makes it easier to remove a catheter without stressing it significantly, the reduced force also means that the catheter is not held in place as strongly. This tradeoff should be considered in selecting whether to include such scoring or not.

Figure 4B:
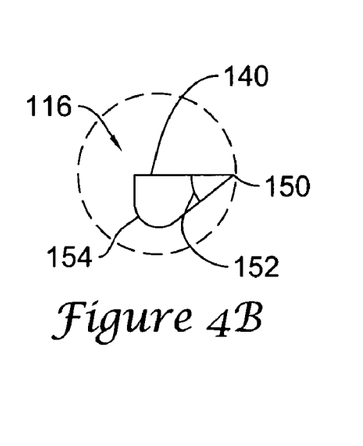
FIG. 4B shows a detail view of an example relatively large tab from FIG. 3.
Figure 4C:
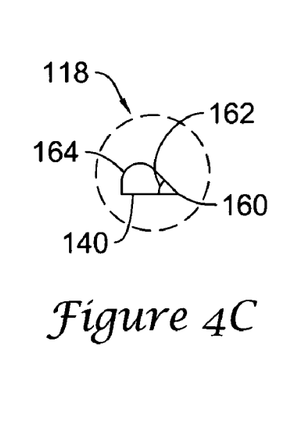
FIG. 4C shows a detail view of an example relatively small tab from FIG. 3.

FIG. 4B shows a detail view of a relatively large tab from FIG. 3. The large tab 116 includes a leading corner 150 defining an angle 152, as well as a second corner 154 and a folding line 140. The second corner 154 can form a vertex of the tab 116 and can have a radius as shown in FIG. 4B. FIG. 4C illustrates the small tab 118 having a leading corner 160, angle 162, a second corner 164, and a folding line 140. The second corner 164 can form a vertex of the tab 118 and can have a radius as shown in FIG. 4C. The large tab 116 and small tab 118 may be generally the same as the tabs shown and explained above with reference to FIGS. 2B-2C. Their orientation may be similar, too.

Figure 4D:
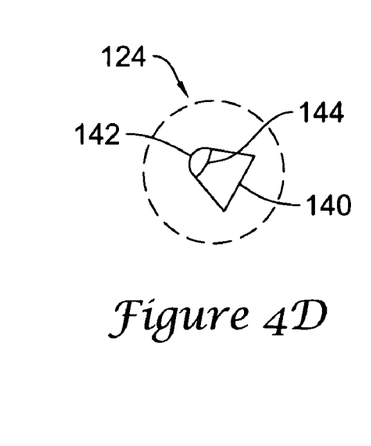
FIG. 4D shows a detail view of an example secondary tab from FIG. 3.

FIG. 4D shows a detail view of a curve tab from FIG. 3. The curve tab 124 is disposed on the catheter holding card to provide support and to secure a curved distal portion of a catheter to the card. The curve tab 124 includes a folding line 140, opposite of which is a radiused angle 142 defining an angle 144. The angle may vary widely, but in some embodiments can be in the range of thirty to fifty degrees. Disposition of the curve tab 124 (location and angle) will depend upon the shape of a particular catheter for which the catheter holding card is designed. The length, from the folding line 140 to the radiused angle 142, may vary as well depending on the location of the curve tab as well as the catheter for which it is used. In an illustrative embodiment, the lengths of tabs on the same catheter holding card may vary from less than a centimeter up to about three centimeters, or more. Further, while the curve tab 124 is shown as an isosceles triangle with a radiused peak, the curve tab may have rectangular, polygonal, or other triangular shapes as well. The locations for curve tabs such as tab 124 may vary depending upon the configuration/shape of the distal curvature of a catheter intended to be packaged on the particular mounting card, as one of skill in the art would understand. In particular, the curve tab 124 would be placed such that it could hold a catheter in position without altering the shape of its distal curvature.

Figures 5, 6:
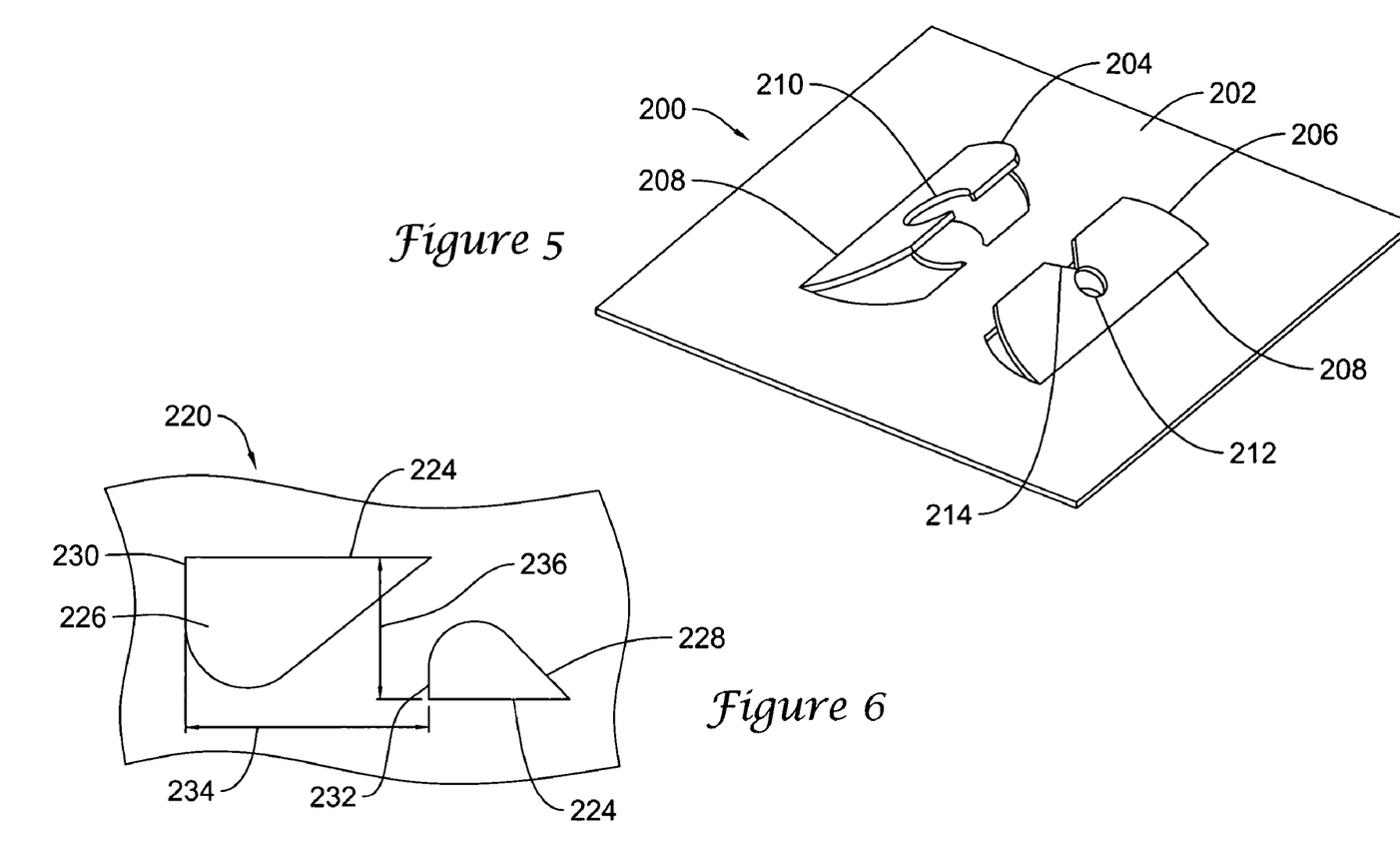
FIG. 5 is a perspective detail view of an illustrative example catheter hub holder.
FIG. 6 is a detail view of an example pairing of a large tab and a small tab.

FIG. 5 is a perspective detail view of an illustrative catheter hub holder. Again, while a circular configuration is shown, other shapes may be used as desired, including oval, polygonal, and combinations of curved/flat edges. The catheter hub holder 200 is shown as being cut out of a generally planar material 202 that is part of a catheter package. As illustrated, the holder 200 includes a first tab 204 and a second tab 206, which are folded up and away from the planar material 202 along fold lines 208. The fold lines 208 may be scored to make folding them along a straight line easier.

The first tab 204 includes a circular cutout 210. The circular cutout 210 may include an opening at its upper end allowing passage of a cylindrical portion of a catheter therein. In use, a catheter will typically be passed into the circular cutout 210 through the opening at a location where the catheter has a lesser diameter, and then moved such that a cylindrical portion of the catheter is in the circular cutout, preventing passage through the opening in the circular cutout. The following sizes are merely illustrative of one embodiment designed for use with a catheter/hub of a certain size, and (particularly the sizes for the circular cutouts 210, 212) may vary depending upon the size of catheter intended for storage/shipping thereon.

In an illustrative embodiment, the fold lines 208 are about 2.5 centimeters apart, each extending for about 2.5 centimeters along the base of the tabs 204, 206. The first tab 204 can be about a centimeter high, with a width near the top of about 1.6 centimeters. The radius of the circular cutout 210 of the first tab 204 can be about 0.33 centimeters. The center of the cutout 210 can be set away from the upper edge of the first tab 204 to create an opening about 0.13 centimeters wide at the upper edge of the first tab 204.

The illustrative second tab 206 has an upper width of about 1.9 centimeters and can be about 0.8 centimeters high. The notch 214 can be formed at a ninety degree angle with an edge set about 2.2 millimeters from the upper edge of the second tab 206. The radius of the circular cutout 212 of the second tab 206 can be about 1.6 millimeters.

FIG. 6 is a detail view of a pairing of a large tab and a small tab. The tab pairing 200 is shown for the purpose of illustrating one example layout for the tabs. On a planar material 222 two tabs are cut and folded out along fold lines 224. The large tab 226 has a trailing edge 230, and the small tab 228 has a trailing edge 232 as well. The distance 234 between the trailing edges 230, 232 can be about 2.5 centimeters. The distance between the fold lines 224 can be about 1.4 centimeters. The sizes for the illustrative tabs correspond to the sizes noted above with reference to in FIGS. 2B and 2C. In particular, the large tab 226 has a length of about 2.6 centimeters, such that its leading corner can be almost even with the trailing edge of the smaller tab. The height of the large tab 224 can be approximately equal to the distance between the fold lines.

Figure 7:
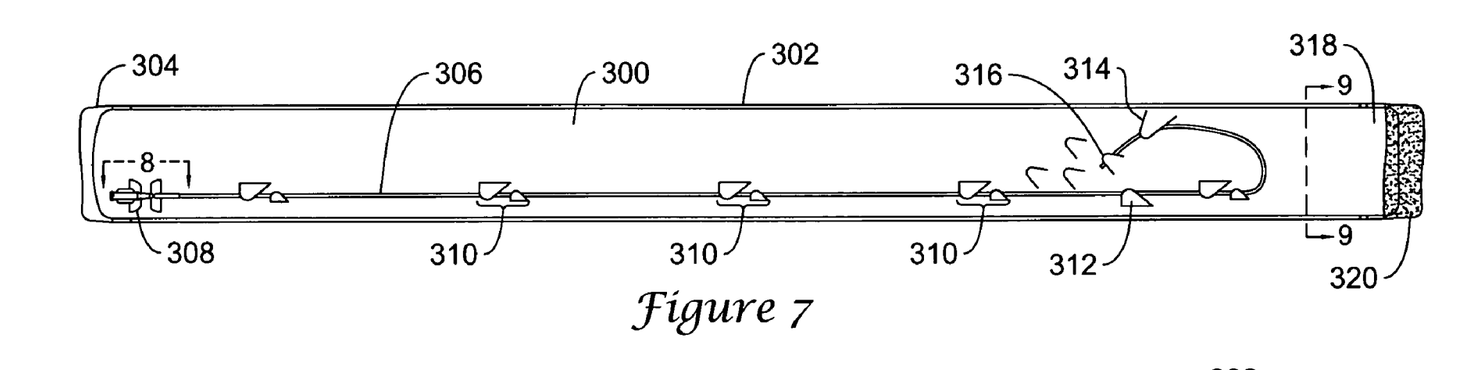
FIG. 7 is an elevation view of an example catheter package holding a catheter and including a sterile barrier thereon.

FIG. 7 is an elevation view of a catheter package holding a catheter and including a sterile barrier thereon. The package includes a mounting card 300 with sides 302 that extend upward, more or less "out" of the page on the elevation drawing. A sterile barrier 304 can be disposed thereover; the sterile barrier may be typically provided as a bag or envelope, but may be simply a wrapped piece. A catheter 306 is disposed on the mounting card 300 inside the sterile barrier 304. The mounting card 300 includes hub holding tabs 308 that hold the hub of the catheter 306. A number of tab pairs 310 hold the shaft of the catheter, while the curved distal end of the catheter is held in place with additional tabs 312, 314, 316. As shown, a portion 318 of the sterile barrier 304 and mounting card 300 extends beyond the end of the sides 302. This distance where the sides 302 are not included may extend, for example, for about 7.5-10.5 cm. In a working example embodiment, this portion 318 extends for about 8.9 cm.

By excluding the sides along this portion 318, the catheter and mounting card 300 may be inserted into a sterile barrier "envelope" that is already sealed along three sides. In particular, the mounting card 300, with a catheter secured thereto, can be inserted, hub end first, into the envelope until the hub end of the mounting card 300 cannot be inserted further. The sterile barrier is sized such that, with the mounting card 300 fully inserted, a portion of the sterile barrier extends beyond the sideless portion 318, as shown at 320 allowing for a seal to be made at that location. The seal may be, for example, a thermal seal, adhesive, mechanical, or any other suitable seal. It should be noted that for the purposes of illustration the sterile barrier 304 is shown as extending by an exaggerated amount beyond the hub end of the mounting card 300 in FIG. 7.

FIG. 8 is a detail view of the catheter hub holder of FIG. 7 taken at location 8 in FIG. 7. As shown, the mounting card 300 includes a first tab 330 and second tab 332. The catheter includes a hub/manifold 334 and a strain relief 336. The first tab 330 secures the hub/manifold 334 at a first, generally cylindrical, location, while the second tab 332 is secured to the strain relief 336, as explained above with reference to FIG. 5. The sterile barrier 304 is shown over, but not necessarily contacting, any of the tabs 330, 332, hub/manifold 334, or strain relief 336.

Figure 9:
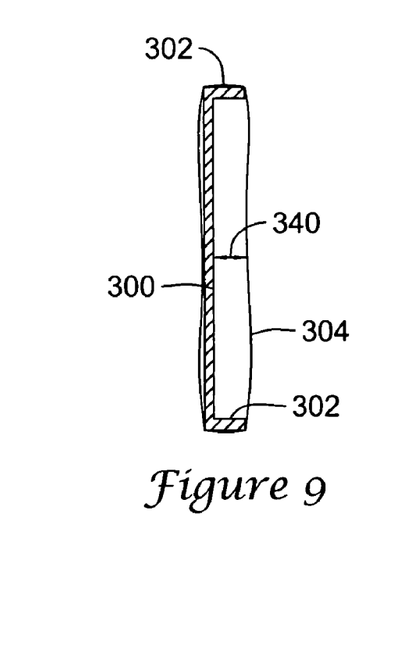
FIG. 9 is a cross sectional view showing the sterile barrier spacer characteristics from FIG. 7.

FIG. 9 is a cross sectional view showing the sterile barrier spacer characteristics from FIG. 7. As shown in FIG. 9, the sides 302 of the mounting card 300 hold the sterile barrier 304 away from the planar portion of the mounting card 300 by a space 340. The space 340, in an illustrative embodiment, can be about 1.1 centimeters wide. This allows room for a canted catheter to retain its curved distal end while encased in the sterile barrier 304 and secured to the mounting card 300. Further, the space 340 makes it easier to remove a catheter from the combination of the sterile barrier and mounting card by eliminating friction, particularly toward the distal end of the catheter, caused by a sterile barrier pressing the catheter against the mounting card 300.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A holding card for holding an elongate medical device and formed of a generally planar piece of material and comprising:
at least one relatively large tab cut into the material; and
at least one relatively small tab cut into the material;
wherein the tabs are placed for holding an elongate medical device and each have:
a leading corner that, when the elongate medical device is held by the tabs, is towards the distal end of the elongate medical device;
a trailing edge that, when the elongate medical device is held by the tabs, is towards the proximal end of the elongate medical device; and
a second, radiused corner defining a vertex of the tab;
wherein the relatively large tab has a generally triangular form creating an angle in the range of about 30-45 degrees at the leading corner, and the relatively small tab has a generally triangular form creating an angle in the range of about 40-50 degrees at the leading corner; and
wherein the tabs are arranged in a plurality of pairs, each pair having one small and one large tab.

2. The holding card of claim 1 wherein the tabs are spaced in pairs such that, with respect to an axial direction of an elongate medical device held therein, the tabs are spaced by about 2.5 centimeters from trailing edge to trailing edge.

3. The holding card of claim 2 wherein the tabs are disposed such that the leading corner of the relatively large tab faces the trailing edge of the relatively small tab.

4. The holding card of claim 1 wherein the relatively large tab has a length of between about 2.3 and 2.7 centimeters.

5. The holding card of claim 1 wherein the relatively large tab has a length of about 2.5 centimeters.

6. The holding card of claim 1 wherein the relatively small tab has a length of between about 1.3 and 1.8 centimeters.

7. The holding card of claim 1 wherein the relatively small tab has a length of about 1.5 centimeters.

8. The holding card of claim 1 wherein the relatively large tab has a length, and wherein the distance along a line passing axially past the relatively large tab and the relatively small tab from the trailing edge of the relatively large tab to the trailing edge of the relatively small tab is about equal to the length of the relatively large tab.

9. The holding card of claim 1 further comprising means for holding a proximal hub of an elongate medical device disposed such that, if an elongate medical device is disposed on the holding card with the hub held in the means for holding a proximal hub, the tabs are located for receiving a portion of the elongate medical device distal of the proximal hub.

10. The holding card of claim 1 further comprising an axially extending scored section along the generally planar piece of material, wherein:
the scored section is placed and the material shaped such that a portion of the planar piece of material near the scored section can be folded outward from the rest of the generally planar piece of material to form a folded portion;
and, when so folded and with an elongate medical device secured to the holding card by the tabs, and when placed within a sterile barrier sheet, the folded portion holds the sterile barrier sheet away from at least a portion of the elongate medical device.

11. The holding card of claim 10 wherein, when the folded portion is formed, the folded portion provides additional rigidity to the generally planar piece of material.

12. The holding card of claim 10 wherein the generally planar piece of material has a hub end and a distal portion end, the large and small tabs being aligned and positioned for receiving an elongate medical device having a hub on the generally planar piece of material such that the hub is received at the hub end, wherein the folded portion does not extend all the way to one of the hub end or the distal portion end.

13. The holding card of claim 1 wherein the relatively large tab creates an angle of about 36-40 degrees.

14. The holding card of claim 1 wherein the relatively large tab creates an angle of about 38 degrees.

15. The holding card of claim 1 wherein the relatively small tab creates an angle of about 43-47 degrees.

16. The holding card of claim 1 wherein the relatively small tab creates an angle of about 45 degrees.

17. The holding card of claim 1 wherein a ratio of the length of the relatively large tab to the length of the relatively small tab yields a ratio in the range of about 1.5 to 1 and 2 to 1.

18. A holding card for holding an elongate medical device and formed of a generally planar piece of material and comprising:
at least one relatively large tab cut into the material; and
at least one relatively small tab cut into the material;
wherein the tabs are placed for holding an elongate medical device and each have:
a leading corner that, when the elongate medical device is held by the tabs, is towards the distal end of the elongate medical device;
a trailing edge that, when the elongate medical device is held by the tabs, is towards the proximal end of the elongate medical device; and
a second, radiused corner defining a vertex of the tab
a first hub holding tab; and
a second hub holding tab;
wherein:
the relatively large tab has a generally triangular form creating an angle in the range of about 30-45 degrees at the leading corner, and the relatively small tab has a generally triangular form creating an angle in the range of about 40-50 degrees at the leading corner;
the tabs are arranged in a plurality of pairs, each pair having one small and one large tab;
the first hub holding tab is a flap of material shaped to receive a first, proximal portion of a hub assembly through a first cutout; and
the second hub holding tab is a flap of material having a notch and a second cutout, the second cutout sized to match a strain relief associated with a hub on an elongate medical device.

19. The holding card of claim 18 wherein the relatively large tab has a length, and wherein the distance along a line passing axially past the relatively large tab and the relatively small tab from the trailing edge of the relatively large tab to the trailing edge of the relatively small tab is about equal to the length of the relatively large tab.

20. The holding card of claim 18 further comprising an axially extending scored section along the generally planar piece of material, wherein:
the scored section is placed and the material shaped such that a portion of the material near the scored section can be folded outward from the rest of the generally planar piece of material to make a folded section;
and, when so folded and with an elongate medical device secured to the catheter holding card by the tabs, and when placed within a sterile barrier sheet, the folded portion holds the sterile barrier sheet away from at least a portion of the elongate medical device.

21. A method of packaging an elongate medical device comprising:
   providing a holding card as defined in claim 18;
   folding the generally planar piece of material along the scored section to create the folded portion; and
   placing an elongate medical device having a hub and a shaft on the generally planar piece of material such that:
   the relatively large and relatively small tabs interact with the shaft; and
   the hub is secured to the first and second hub holding tabs.

22. A method as in claim 21 further comprising placing a sterile barrier over the holding card and elongate medical device such that the sterile barrier is suspended over the catheter by the folded portions.

23. A method as in claim 22 wherein:
   the folded portions extend along a part of the holding card but end prior to an end of the holding card opposite the end of the holding card at which the hub holding tabs are located;
   the sterile barrier comprises an envelope having an opening, the step of placing the sterile barrier over the holding card and elongate medical device including:
   putting the holding card and elongate medical device inside the sterile barrier through the opening by advancing the end of the holding card having the hub holding tabs into the opening first and then advancing the rest of the holding card therethrough; and
   sealing the opening.

24. The method of claim 21 wherein the holding card has a first rigidity before the step of folding is performed, and wherein the holding card has a second rigidity greater than the first rigidity after the step of folding.

25. A method of packaging an elongate medical device:
   providing a generally planar holding card having a first surface;
   cutting a number of relatively small tabs in the holding card;
   cutting a number of relatively large tabs larger than the small tabs in the holding card;
   wherein the tabs are placed for holding the elongate medical device and each have:
   a leading corner that, when the elongate medical device is held by the tabs, is towards the distal end of the elongate medical device;
   a trailing edge that, when the elongate medical device is held by the tabs, is towards the proximal end of he elongate medical device; and
   a second, radiused corner defining a vertex of the tab;
   wherein the tabs are arranged in a plurality of pairs, each pair having one small and one large tab;
   pushing one of the small tabs upward with respect to the first surface causing the small tab to deflect away from the first surface, then passing a portion of a catheter shaft under the small tab, and allowing the small tab to deflect back toward the first surface; and
   pushing one of the large tabs upward with respect to the first surface causing the large tab to deflect away from the first surface, then passing a portion of a catheter shaft under the large tab, and allowing the large tab to deflect back toward the first surface.

26. Packaging for an elongate medical device comprising:
   a generally planar piece of material having a surface and including a first end and a second end;
   a relatively large tab disposed along the surface of the material, the relatively large tab including a generally triangular form including a leading corner creating an angle in the range of about 30-45 degrees, a radiused second corner defining a vertex of the tab, and a trailing edge; and
   a relatively small tab disposed along the surface of the material, the relatively small tab having a generally triangular form including a leading corner creating an angle in the range of about 40-50 degrees, radiused second corner defining a vertex of the tab, and a trailing edge;
   wherein the tabs are disposed along the surface such that the leading corners of the tabs are oriented towards the first end of the material, and the trailing edges of the tabs are oriented towards the second end of the material, and wherein the tabs are arranged in a plurality of pairs of one small and one large tab.

27. A method of making packaging for an elongate medical device, the packaging including a first end and a second end, the method comprising:
   providing a generally planar piece of material having a surface;
   cutting at least one relatively large tab into the surface of the material, the relatively large tab including a generally triangular form including a leading corner creating an angle in the range of about 30-45 degrees, a radiused second corner defining a vertex of the tab, and a trailing edge; and
   cutting at least one relatively small tab into surface of the material, the relatively small tab having a generally triangular form including a leading corner creating an angle in the range of about 40-50 degrees, a radiused second corner defining a vertex of the tab, and a trailing edge;
   wherein the tabs cut into the surface such that the leading corners of the tabs are oriented towards the first end of the packaging; and the trailing edges of the tabs are oriented towards the second end of the packaging, and wherein the tabs are arranged in a plurality of pairs of one small and one large tab.

* * * * *